United States Patent [19]

Mebes et al.

[11] Patent Number: 4,845,256

[45] Date of Patent: Jul. 4, 1989

[54] PRODUCTION OF SILYL QUATERNARY AMMONIUM COMPOUNDS

[75] Inventors: Bruno Mebes, Burgdorf; Christine Lüdi, Uetendorf-Allmend, both of Switzerland

[73] Assignee: Sanitized Ag, Burgdorf, Switzerland

[21] Appl. No.: 186,279

[22] Filed: Apr. 26, 1988

Related U.S. Application Data

[63] Continuation-in-part of Ser. No. 138,632, Dec. 28, 1987, abandoned, which is a continuation of Ser. No. 45,917, May 1, 1987, abandoned.

[30] Foreign Application Priority Data

May 2, 1986 [CH] Switzerland ............... 1810/86

[51] Int. Cl.$^4$ .................. C07F 7/10; C07F 7/18
[52] U.S. Cl. .................................. 556/413
[58] Field of Search ........................... 556/413

[56] References Cited

U.S. PATENT DOCUMENTS

| | | | |
|---|---|---|---|
| 2,715,133 | 8/1955 | Speier | 556/413 |
| 3,560,385 | 2/1971 | Roth | 252/49.6 |
| 3,587,178 | 1/1971 | gölitz et al. | 556/413 |
| 3,661,963 | 5/1972 | Pepe et al. | 556/413 |
| 3,794,736 | 2/1974 | Abbott et al. | 556/413 X |
| 3,817,739 | 6/1974 | Abbott et al. | 556/413 X |
| 4,282,366 | 8/1981 | Eudy | 556/413 |

FOREIGN PATENT DOCUMENTS

| | | | |
|---|---|---|---|
| 0615086 | 1/1986 | Japan | 556/413 |
| 1153824 | 5/1969 | United Kingdom | 556/413 X |

OTHER PUBLICATIONS

Thoicheimer, "Synthetic Methods of Organic Chemistry", vol. 24, p. 205 (1970).

*Primary Examiner*—Paul F. Shaver
*Attorney, Agent, or Firm*—Gerald D. Sharkin; Richard E. Vila; Thomas C. Doyle

[57] ABSTRACT

The invention relates to a process for the production of silyl quaternary ammonium compounds comprising reacting a tertiary amine with a trialkoxy silane in the presence of a catalytic amount of an alkali metal or earth alkali metal iodide. The resulting compounds can be used directly without a further purification step.

20 Claims, No Drawings

PRODUCTION OF SILYL QUATERNARY AMMONIUM COMPOUNDS

This application is a continuation-in-part of application Ser. No. 07/138,632, filed Dec. 28, 1987, and now abandoned, which is a continuation of application Ser. No. 07/045,917, filed May 1, 1987, now abandoned.

The invention relates to a process for the production of silyl quaternary ammonium compounds useful as bacteriostatic and fungistatic agents for textiles and other substrates.

It is well known that silyl quanternary ammonium compounds possess significant antimicrobial properties and are largely used as disinfectants. They have various interesting properties which render them particularly valuable; they are rapidly effective due to their surface activity; they demonstrate bacteriostatic, fungistatic and algistatic properties of a high level; they have a relatively low toxicity and do not cause irritations, particularly skin irritation; they are biodegradable and odourless; they are stable to storage and not influenced by hard water; they are combinable with other biocidal agents and are chemically bonded to a variety of textiles and other surfaces, thus imparting durable bacteriostatic and fungistatic properties.

While these compounds have interesting properties, their preparation is rather long and complicated. It has now been found that they can be prepared with a higher degree of purity in a significantly shorter time period than in the hitherto known processes.

Accordingly, there is provided a process for the production of a compound of formula I

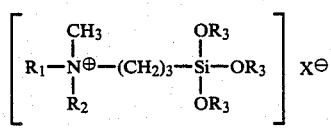

in which
$R_1$ is linear $C_{8-16}$ alkyl,
$R_2$ is methyl or linear $C_{8-16}$ alkyl
each $R_3$, independently, is methyl, ethyl, propyl or butyl, and
$X^\ominus$ is an anion,
comprising reacting a tertiary amine of formula II

in which $R_1$ and $R_2$ are as defined above with a silane of formula III

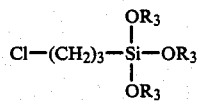

in which $R_3$ is as defined above, in the presence of a catalytic amount of an alkali metal or earth alkali metal iodide, and, if desired, replacing the halogen ion with another anion.

$R_1$ is preferably linear octyl, nonyl, decyl or dodecyl, more preferably n-decyl.

$R_2$ is preferably methyl or identical to $R_1$. More preferably $R_2$ is methyl or n-decyl.

Preferred alkali metal iodide used as catalytic agent in the process of the invention is sodium or potassium iodide, particularly sodium iodide. Preferably the alkali metal or earth alkali metal iodide is used in an amount of 5–50 mol %, particularly 5–15 mol %, based on the amine of formula II.

Preferred earth alkali metal iodide is magnesium iodide which is added as a fine dispersion.

The amine of formula II is advantageously reacted with the silane of formula III in a stoichiometric mol ratio preferably using a slight excess of the silane. Typically, the reactants are used in a mole ratio of silance to amine in the range 1–1.1:1, preferably 1–1.05:1.

According to a particularly preferred embodiment of the process of the invention, the amine of formula II is used in a mole ratio to the silane of formula III and the alkali metal iodide of 1:1.05:0.1.

The reaction of the amine of formula II with the silane of formula III in the presence of the alkali metal or earth alkali metal iodide is preferably carried out in an organic solvent such as a $C_{2-4}$ glycol mono-($C_{1-4}$alkyl)ether or a lower alcohol, for example ethylene, propylene or butylene glycol mono-($C_{1-4}$ alkyl)ether, methanol, ethanol, propanol or isopropanol. The preferred solvent is propylene glycol monomethyl ether. The solvent, when present, is advantageously used in a weight ratio to the total weight of the reactants of 0.8–1.2:1, preferably 0.85–1:1. In the case of earth alkali metal iodide being used as catalytic agent, an earth alkali metal chloride is obtained which precipitates and can be filtered off.

The process of the invention is advantageously effected within a temperature range of 80° to 120° C., preferably at about 100° C.

Duration of the reaction will vary with the particular reaction conditions. When an alkali metal iodide is used, particularly in an amount of 10 mol % based on the amine of formula II, the reaction time is from 8 to 9 hours. When an earth alkali metal iodide is employed, reaction times are about 30 to 36 hours.

The reaction between the amine of formula II and the silane of formula III as disclosed above yields a compound of formula I in which $X^\ominus$ is at least predominantly chloride. The resulting compound of formula I may also be obtained as a mixed halogenide in which a major part of $X^\ominus$ is chloride and a small part is iodide, particularly when an earth alkali metal is used. If desired, the resulting halogenide of formula I may be converted according to known methods into a salt in which the cationic charge is balanced with another anion. Suitable anions as $X^\ominus$ other than $Cl^-$ and $I^\ominus$, include for example the fluoride, sulphate, acetate or phosphate anion or anion equivalent.

One advantageous aspect of the process of the invention is the significant reduction of the reaction time. Furthermore, the resulting silyl quaternary ammonium compounds of formula I are obtained in significantly higher purity and can be used directly without any further purification step. Thus, when the reaction is carried out in a solvent as disclosed above, the reaction is complete after 8 to 9 hours and the resulting reaction mixture can be used as such after filtration and, if required, can be further diluted to the desired concentration for use. In the process of the invention, the side reactions leading to the scission of alkoxy groups and to polymerisation, which normally occur in the hitherto known processes are substantially hindered. As no purification step of the final product is required, the total yield of the process of the invention is high.

The following Examples illustrate the invention. All the temperatures are in degrees Centigrade.

EXAMPLE 1

35.1 g Propylene glycol monomethylether are introduced in a reaction vessel purged with a nitrogen stream. Then 1.5 g (0.01 M) sodium iodide are added at room temperature with vigrous stirring. After dissolution of the sodium iodide, 21.5 g (0.108 M) 3-chloropropyl trimethoxy silane are added. A slightly yellow precipitate is formed. The reaction mixture is heated to 100° and, after addition of 18.7 g (0.1 M) decyldimethylamine at 100°, the whole is stirred for 8–9 hours at this temperature.

Thereafter the reaction mixture is cooled to 15° and the precipitated salt is filtered. The resulting clear, slightly viscous, orange-yellow filtrate is a 40–50% by weight solution of 3-(trimethoxy silyl)propyl-decyl-dimethyl-ammonium chloride which can be further diluted to the desired concentration and used as such.

EXAMPLES 2 to 56

By following the procedure of Example 1 and using the appropriate starting amines and silanes, further silyl quaternary ammonium compounds as listed below can be obtained.

3-(trimethoxysilyl)propyl-di-n-octylmethyl-ammonium chloride
3-(trimethoxysilyl)propyl-n-octyldimethyl-ammonium chloride
3-(trimethoxysilyl)propyl-di-n-nonylmethyl-ammonium chloride
3-(trimethoxysilyl)propyl-n-nonyldimethyl-ammonium chloride
3-(trimethoxysilyl)propyl-di-decylmethyl-ammonium chloride
3-(trimethoxysilyl)propyl-di-n-undecylmethyl-ammonium chloride
3-(trimethoxysilyl)propyl-n-undecyldimethyl-ammonium chloride
3-(trimethoxysilyl)propyl-di-n-dodecylmethyl-ammonium chloride
3-(trimethoxysilyl)propyl-n-dodecyldimethyl-ammonium chloride
3-(trimethoxysilyl)propyl-di-n-tridecyldimethyl-ammonium chloride
3-(trimethoxysilyl)propyl-n-tridecyldimethyl-ammonium chloride
3-(trimethoxysilyl)propyl-di-n-tetradecylmethyl-ammonium chloride
3-(trimethoxysilyl)propyl-n-tetradecyldimethyl-ammonium chloride
3-(triethoxysilyl)propyl-di-n-octylmethyl-ammonium chloride
3-(triethoxysilyl)propyl-n-octyldimethyl-ammonium chloride
3-(triethoxysilyl)propyl-di-n-nonylmethyl-ammonium chloride
3(triethoxysilyl)propyl-n-nonyldimethyl-ammonium chloride
3-(triethoxysilyl)propyl-di-n-decylmethyl-ammonium chloride
3-(triethoxysilyl)propyl-n-decyldimethyl-ammonium chloride
3-(triethoxysilyl)propyl-di-n-undecylmethyl-ammonium chloride
3-(triethoxysilyl)propyl-n-undecyldimethyl-ammonium chloride
3-(triethoxysilyl)propyl-di-n-dodecylmethyl-ammonium chloride
3-(triethoxysilyl)propyl-n-dodecyldimethyl-ammonium chloride
3-(triethoxysilyl)propyl-di-n-tridecylmethyl-ammonium chloride
3-(triethoxysilyl)propyl-n-tridecyldimethyl-ammonium chloride
3-(triethoxysilyl)propyl-di-n-tetradecylmethyl-ammonium chloride
3-(triethoxysilyl)propyl-n-tetradecyldimethyl-ammonium chloride
3-(tripropoxysilyl)propyl-di-n-octylmethyl-ammonium chloride
3-(tripropoxysilyl)propyl-n-octyldimethyl-ammonium chloride
3-(tripropoxysilyl)propyl-di-n-nonylmethyl-ammonium chloride
3-(tripropoxysilyl)propyl-n-nonyldimethyl-ammonium chloride
3-(tripropoxysilyl)propyl-di-n-decylmethyl-ammonium chloride
3-(tripropoxysilyl)propyl-n-decyldimethyl-ammonium chloride
3-(tripropoxysilyl)propyl-di-n-undecylmethyl-ammonium chloride
3-(tripropoxysilyl)propyl-n-undecyldimethyl-ammonium chloride
3-(tripropoxysilyl)propyl-di-n-dodecylmethyl-ammonium chloride
3-(tripropoxysilyl)propyl-n-dodecyldimethyl-ammonium chloride
3-(tripropoxysilyl)propyl-di-n-tridecylmethyl-ammonium chloride
3-(tripropoxysilyl)propyl-n-tridecyldimethyl-ammonium chloride
3-(tripropoxysilyl)propyl-di-n-tetradecylmethyl-ammonium chloride
3-(tripropoxysilyl)propyl-n-tetradecyldimethyl-ammonium chloride
3-(tributoxysilyl)propyl-di-n-octylmethyl-ammonium chloride
3-(tributoxysilyl)propyl-n-octyldimethyl-ammonium chloride
3-(tributoxysilyl)propyl-di-n-nonylmethyl-ammonium chloride
3-(tributoxysilyl)propyl-n-nonyldimethyl-ammonium chloride
3-(tributoxysilyl)propyl-di-n-decylmethyl-ammonium chloride
3-(tributoxysilyl)propyl-n-decyldimethyl-ammonium chloride
3-(tributoxysilyl)propyl-di-n-undecylmethyl-ammonium chloride
3-(tributoxysilyl)propyl-n-undecyldimethyl-ammonium chloride
3-(tributoxysilyl)propyl-di-n-dodecylmethyl-ammonium chloride
3-(tributoxysilyl)propyl-n-dodecyldimethyl-ammonium chloride
3-(tributoxysilyl)propyl-di-n-tridecylmethyl-ammonium chloride
3-(tributoxysilyl)propyl-n-tridecyldimethyl-ammonium chloride 3-(tributoxysilyl)propyl-di-n-tetradecylmethyl-ammonium chloride, and
3-(tributoxysilyl)propyl-n-tetradecyldimethyl-ammonium chloride.

EXAMPLE 57

35.1 g Propylen-glycol-monomethylether are placed in a reaction vessel, purged with a nitrogen stream.

Then 2.77 g (0.01 M) magnesium-iodide, as a fine powder is added to the solvent with vigorous stirring. The dispersion is heated up to 100° C. and 21.5 g (0.108 M) 3-chloropropyl-trimethoxy-silane are added under continuous stirring. The dispersion turns slightly yellow. After heating up to 85°–90° C. 18.7 g (0.1 M) decyldimethylamine are added. The temperature is brought up to the boiling point and the mixture is kept for 32 hours at 120° C. under reflux. The reaction-mixture is cooled to 20° C., filtered from the magnesium-chloride and the product results with a quaternary amine content of 24–45% by weight.

What is claimed is:

1. A process for the production of a compound of formula I

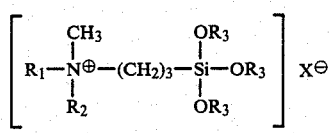

in which
   $R_1$ is linear $C_{8-16}$ alkyl,
   $R_2$ is methyl or linear $C_{8-16}$ alkyl
   each $R_3$, independently, is methyl, ethyl, propyl or butyl, and
   $X^\ominus$ is an anion,
comprising reacting a tertiary amine of formula II

in which $R_1$ and $R_2$ are as defined above with a silane of formula III

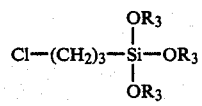

in which $R_3$ is as defined above,
in the presence of a catalytic amount of an iodide or earth iodide iodide.

2. A process according to claim 1, in which the alkali metal or earth alkali metal iodide is sodium iodide or potassium iodide.

3. A process according to claim 1, in which the alkali metal or earth alkali metal iodide is used in an amount of 5–50 mol % based on the amine of formula II.

4. A process according to claim 1, in which the alkali metal or earth alkali metal iodide is used in an amount of 5–15 mol % based on the amine of formula II.

5. A process according to claim 1, in which the silane of formula III is used in a mole ratio to the amine of formula II of 1.05:1.

6. A process according to claim 1, in which the amine of formula II is used in a mole ratio to the silane of formula III and the alkali metal iodide of 1:1.05:0.1.

7. A process according to claim 1, in which the reaction is carried out in an organic solvent.

8. A process according to claim 1, in which the reaction is carried out in a $C_{2-4}$ glycol mono-($C_{1-4}$ alkyl)ether or a lower alcohol.

9. A process according to claim 1, in which the reaction is carried out in propyleneglycol monomethyl ether.

10. A process according to claim 1, in which the reaction is carried out in an organic solvent in an amount corresponding to the total weight of the reactants.

11. A process according to claim 3 which is effected at a temperature in the range 80° to 120° C.

12. A process according to claim 3 wherein $R_1$ is octyl, nonyl, decyl or dodecyl and $R_2$ is methyl or identical to $R_1$.

13. A process according to claim 3 wherein the mol ratio of silane of formula III to amine of formula II is in the range 1–1.1:1.

14. A process according to claim 4 in which the mol ratio of silane of formula III to amine of formula II is 1.05:1.

15. A process according to claim 11 in which the mol ratio of silane of formula III to amine of formula II is in the range 1–1.1:1.

16. A process according to claim II in which the alkali metal iodide or earth alkali metal iodide is sodium iodide or potassium iodide.

17. A process according to claim 15 in which the alkali metal iodide is or earth alkali metal iodide is sodium iodide or potassium iodide.

18. A process according to claim 15 in which $R_1$ is n-decyl and $R_2$ is methyl or n-decyl.

19. A process according to claim 17 in which $R_1$ is n-decyl and $R_2$ is methyl or n-decyl.

20. A process according to claim 19 which is carried out in the presence of an organic solvent selected from the group consisting of methanol, ethanol, propanol, isopropanol and mono-($C_{1-4}$alkyl)ethers of ethylene, propylene and butylene glycol.

* * * * *